US006375986B1

(12) United States Patent
Ryde et al.

(10) Patent No.: US 6,375,986 B1
(45) Date of Patent: Apr. 23, 2002

(54) SOLID DOSE NANOPARTICULATE COMPOSITIONS COMPRISING A SYNERGISTIC COMBINATION OF A POLYMERIC SURFACE STABILIZER AND DIOCTYL SODIUM SULFOSUCCINATE

(75) Inventors: Niels P. Ryde, Malvern; Stephen B. Ruddy, Schwenksville, both of PA (US)

(73) Assignee: Elan Pharma International Ltd., Clare (IE)

( * ) Notice: Subject to any disclaimer, the term of this patent is extended or adjusted under 35 U.S.C. 154(b) by 0 days.

(21) Appl. No.: 09/666,539

(22) Filed: Sep. 21, 2000

(51) Int. Cl.$^7$ .............................. A61K 9/14; A61K 9/20; A61K 9/46

(52) U.S. Cl. ....................... 424/489; 424/466; 424/464; 424/434; 424/44; 424/43; 514/535

(58) Field of Search ................................. 424/489, 466, 424/464, 434, 44, 43; 514/535

(56) References Cited

U.S. PATENT DOCUMENTS

| | | | |
|---|---|---|---|
| 4,783,484 A | 11/1988 | Violante et al. ............. 514/535 |
| 4,826,689 A | 5/1989 | Violante et al. ............. 424/489 |
| 4,997,454 A | 3/1991 | Violante et al. ........... 23/305 A |
| 5,145,684 A | 9/1992 | Liversidge et al. .......... 424/489 |
| 5,298,262 A | 3/1994 | Na et al. ..................... 424/489 |
| 5,302,401 A | 4/1994 | Liversidge et al. .......... 424/501 |
| 5,318,767 A | 6/1994 | Liversidge et al. ............. 424/4 |
| 5,326,552 A | 7/1994 | Na et al. ......................... 424/4 |
| 5,336,507 A | 8/1994 | Na et al. ..................... 424/489 |
| 5,346,702 A | 9/1994 | Na et al. ..................... 424/490 |
| 5,352,459 A | 10/1994 | Hollister et al. ............. 424/489 |
| 5,399,363 A | 3/1995 | Lifersidge et al. ........... 424/490 |
| 5,401,492 A | 3/1995 | Kellar et al. ..................... 424/9 |
| 5,429,824 A | 7/1995 | June ............................. 424/489 |
| 5,447,710 A | 9/1995 | Na et al. .................. 424/9.455 |
| 5,451,393 A | 9/1995 | Liversidge et al. ......... 424/9.45 |
| 5,466,433 A | 11/1995 | Bacon et al. ............. 424/9.451 |
| 5,466,440 A | 11/1995 | Ruddy et al. ............. 424/9.411 |
| 5,470,583 A | 11/1995 | Na et al. ..................... 424/489 |
| 5,472,683 A | 12/1995 | Illig .......................... 424/9.45 |
| 5,494,683 A | 2/1996 | Liversidge et al. .......... 424/490 |
| 5,500,204 A | 3/1996 | Osifo ....................... 424/9.453 |
| 5,503,723 A | 4/1996 | Ruddy et al. ................ 204/450 |
| 5,510,118 A | 4/1996 | Bosch et al. ................. 424/489 |
| 5,518,738 A | 5/1996 | Eickhoff et al. ............. 424/493 |
| 5,521,218 A | 5/1996 | Osifo ........................... 514/533 |
| 5,525,328 A | 6/1996 | Bacon et al. ............... 424/9.45 |
| 5,534,270 A | 7/1996 | De Castro .................. 424/490 |
| 5,543,133 A | 8/1996 | Swanson et al. ........... 424/9.45 |
| 5,552,160 A | 9/1996 | Liversidge et al. .......... 424/489 |
| 5,560,931 A | 10/1996 | Eichoff et al. ............... 424/489 |
| 5,560,932 A | 10/1996 | Bagchi et al. ............... 424/489 |
| 5,565,188 A | 10/1996 | Wong et al. ............. 424/9.411 |
| 5,571,536 A | 11/1996 | Eickhoff et al. ............. 424/489 |
| 5,573,749 A | 11/1996 | Illig .......................... 424/9.45 |

(List continued on next page.)

FOREIGN PATENT DOCUMENTS

| | | |
|---|---|---|
| WO | 96/25918 | 8/1996 |
| WO | 98/35666 | 8/1998 |
| WO | 00/18374 | 4/2000 |
| WO | 00/27363 | 5/2000 |

*Primary Examiner*—Diana Dudash
*Assistant Examiner*—Mina Haghighation
(74) *Attorney, Agent, or Firm*—Foley & Lardner (57) ABSTRACT

Disclosed are solid dose nanoparticulate compositions comprising a poorly soluble active agent, at least one polymeric surface stabilizer, and dioctyl sodium sulfosuccinate (DOSS). The solid dose compositions exhibit superior redispersibility of the nanoparticulate composition upon administration to a mammal, such as a human or animal. The invention also describes methods of making and using such compositions.

34 Claims, 1 Drawing Sheet

FIGURE 1: Plasdone S630 + DOSS

U.S. PATENT DOCUMENTS

| | | | |
|---|---|---|---|
| 5,573,750 A | 11/1996 | Singh | 424/9.45 |
| 5,580,579 A | 12/1996 | Ruddy et al. | 424/489 |
| 5,585,108 A | 12/1996 | Ruddy et al. | 424/434 |
| 5,587,143 A | 12/1996 | Wong | 424/9.1 |
| 5,593,657 A | 1/1997 | Ruddy et al. | 424/9.41 |
| 5,603,916 A | 2/1997 | Singh | 424/9.45 |
| 5,628,981 A | 5/1997 | Liversidge et al. | 424/94 |
| 5,643,552 A | 7/1997 | Illig | 424/9.45 |
| 5,665,330 A | 9/1997 | Wong | 424/9.44 |
| 5,665,331 A | 9/1997 | Bagchi et al. | 424/9.45 |
| 5,668,196 A | 9/1997 | Robinson et al. | 424/9.451 |
| 5,670,136 A | 9/1997 | Bacon et al. | 424/9.455 |
| 5,716,642 A | 2/1998 | Bagchi et al. | 424/489 |
| 5,718,919 A | 2/1998 | Ruddy et al. | 424/489 |
| 5,741,522 A | 4/1998 | Violante et al. | 424/489 |
| 5,747,001 A | 5/1998 | Wiedmann et al. | 424/45 |
| 5,776,496 A | 7/1998 | Violante et al. | 424/489 |
| 5,834,025 A | 11/1998 | De Garavilla et al. | 424/501 |
| 6,045,829 A | 4/2000 | Liversidge et al. | 424/489 |
| 6,068,858 A | 5/2000 | Liversidge et al. | 424/489 |
| 6,165,506 A * | 12/2000 | Jain et al. | 424/466 |

* cited by examiner

SOLID DOSE NANOPARTICULATE COMPOSITIONS COMPRISING A SYNERGISTIC COMBINATION OF A POLYMERIC SURFACE STABILIZER AND DIOCTYL SODIUM SULFOSUCCINATE

FIELD OF THE INVENTION

The present invention is directed to solid dose nanoparticulate compositions having a synergistic combination of at least one polymeric surface stabilizer and dioctyl sodium sulfosuccinate (DOSS). The solid dose compositions exhibit superior redispersion of the nanoparticulate composition either upon administration to a mammal, such as a human or animal, or reconstitution in an aqueous electrolyte solution.

BACKGROUND OF THE INVENTION

A. Background Regarding Nanoparticulate Compositions

Nanoparticulate compositions, first described in U.S. Pat. No. 5,145,684 ("the '684 patent"), are particles consisting of a poorly soluble therapeutic or diagnostic agent having adsorbed onto the surface thereof a non-crosslinked surface stabilizer. This invention is an improvement over that disclosed in the '684 patent, as the '684 patent does not describe the use of synergistic combinations of polymeric surface stabilizers and DOSS in solid dose compositions.

Prior U.S. patents teach the use of DOSS as a primary or secondary surface stabilizer for nanoparticulate compositions. See e.g., U.S. Pat. No. 5,145,684, for "Surface Modified Drug Nanoparticles;" U.S. Pat. No. 5,302,401, for "Method to Reduce Particle Size Growth During Lyophilization;" U.S. Pat. No. 5,318,767, for "X-Ray Contrast Compositions Useful in Medical Imaging;" U.S. Pat. No. 5,336,507, for "Use of Charged Phospholipids to Reduce Nanoparticle Aggregation;" U.S. Pat. No. 5,346,702, for "Use of Non-Ionic Cloud Point Modifiers to Minimize Nanoparticulate Aggregation During Sterilization;" U.S. Pat. No. 5,399,363, for "Surface Modified Anticancer Nanoparticles;" U.S. Pat. No. 5,401,492, for "Water-Insoluble Non-Magnetic Manganese Particles as Magnetic Resonance Enhancement Agents;" U.S. Pat. No. 5,429,824, for "Use of Tyloxapol as a Nanoparticulate Stabilizer;" U.S. Pat. No. 5,451,393, for "X-Ray Contrast Compositions Useful in Medical Imaging;" U.S. Pat. No. 5,466,440, for "Formulations of Oral Gastrointestinal Diagnostic X-Ray Contrast Agents in Combination with Pharmaceutically Acceptable Clays;" U.S. Pat. No. 5,470,583, for "Method of Preparing Nanoparticle Compositions Containing Charged Phospholipids to Reduce Aggregation;" U.S. Pat. No. 5,494,683, for "Surface Modified Anticancer Nanoparticles;" U.S. Pat. No. 5,503,723, for "Isolation of Ultra Small Particles;" U.S. Pat. No. 5,510,118, for "Process for Preparing Therapeutic Compositions Containing Nanoparticles;" U.S. Pat. No. 5,543,133, for "Process of Preparing X-Ray Contrast Compositions Containing Nanoparticles;" U.S. Pat. No. 5,552,160, for "Surface Modified NSAID Nanoparticles;" U.S. Pat. No. 5,560,931, for "Formulations of Compounds as Nanoparticulate Dispersions in Digestible Oils or Fatty Acids;" U.S. Pat. No. 5,560,932, for "Microprecipitation of Nanoparticulate Pharmaceutical Agents;" U.S. Pat. No. 5,571,536, for "Formulations of Compounds as Nanoparticulate Dispersions in Digestible Oils or Fatty Acids;" U.S. Pat. No. 5,580,579, for "Site-Specific Adhesion Within the GI Tract Using Nanoparticles Stabilized by High Molecular Weight, Linear Poly(ethylene Oxide) Polymers;" U.S. Pat. No. 5,587,143, for "Butylene Oxide-Ethylene Oxide Block Copolymer Surfactants as Stabilizer Coatings for Nanoparticulate Compositions;" U.S. Pat. No. 5,593,657, for "Novel Barium Salt Formulations Stabilized by Non-Ionic and Anionic Stabilizers;" U.S. Pat. No. 5,628,981, for "Improved Formulations of Oral Gastrointestinal Diagnostic X-Ray Contrast Agents and Oral Gastrointestinal Therapeutic Agents;" U.S. Pat. No. 5,665,331, for "Co-Microprecipitation of Nanoparticulate Pharmaceutical Agents with Crystal Growth Modifiers;" U.S. Pat. No. 5,716,642, for "Microprecipitation of Nanoparticulate Pharmaceutical Agents Using Surface Active Material Derived from Similar Pharmaceutical Agents;" U.S. Pat. No. 5,718,919, for "Nanoparticles Containing the R(–) Enantiomer of Ibuprofen;" U.S. Pat. No. 5,747,001, for "Aerosols Containing Beclomethasone Nanoparticle Dispersions;" U.S. Pat. No. 5,834,025, for "Reduction of Intravenously Administered Nanoparticulate Formulation Induced Adverse Physiological Reactions;" U.S. Pat. No. 6,045,829, for "Nanocrystalline Formulations of Human Immunodeficiency Virus (HIV) Protease Inhibitors Using Cellulosic Surface Stabilizers;" and U.S. Pat. No. 6,068,858, for "Methods of Making Nanocrystalline Formulations of Human Immunodeficiency Virus (HIV) Protease Inhibitors Using Cellulosic Surface Stabilizers." In addition, several published international applications teach the usefulness of DOSS as a primary or secondary surface stabilizer for nanoparticulate compositions. See e.g., WO 98/35666, for "Formulations of Nanoparticle Naproxen Tablets;" WO 00/18374, for "Controlled Release Nanoparticulate Compositions;" WO 96/25918, for "Aerosols Containing Nanoparticulate Dispersions;" and WO 00/27363, for "Aerosols Comprising Nanoparticle Drugs."

Prior art patents also teach the use of DOSS as a cloud point modifier for nanoparticulate surface stabilizers. See e.g., U.S. Pat. No. 5,298,262, for "Use of Ionic Cloud Point Modifiers to Prevent Particle Aggregation During Sterilization;" U.S. Pat. No. 5,326,552, for "Novel Formulation for Nanoparticulate X-Ray Blood Pool Contrast Agents Using High Molecular Weigh Non-ionic Surfactants;" U.S. Pat. No. 5,346,702, for "Use of Non-Ionic Cloud Point Modifiers to Minimize Nanoparticulate Aggregation During Sterilization;" U.S. Pat. No. 5,352,459, for "Use of Purified Surface Modifiers to Prevent Particle Aggregation During Sterilization;" U.S. Pat. No. 5,447,710, for "Method for Making Nanoparticulate X-Ray Blood Pool Contrast Agents Using High Molecular Weight Non-Ionic Surfactants;" U.S. Pat. No. 5,565,188, for "Polyalkylene Block Copolymers as Surface Modifiers for Nanoparticles;" U.S. Pat. No. 5,665,330, for "Dual Purpose Diagnostic/Therapeutic Agent Having a Tri-Iodinated Benzoyl Group Linked to a Coumarin."

And several prior art references teach the use of DOSS in nanoparticulate compositions as both a surface stabilizer and as a cloud point modifier for a primary surface stabilizer. See e.g., U.S. Pat. No. 5,466,433, for "Polyiodinated Aroyloxy Esters;" U.S. Pat. No. 5,472,683, for "Nanoparticle Mixed Carbamic Anhydrides as X-Ray Contrast Agents for Blood Pool and Lymphatic System Imaging;" U.S. Pat. No. 5,500,204, for "Nanoparticulate Diagnostic Dimers as X-Ray Contrast Agents for Blood Pool and Lymphatic System Imaging;" U.S. Pat. No. 5,521,218, for "Nanoparticulate Iododipamide Derivatives for Use as X-Ray Contrast Agents;" U.S. Pat. No. 5,525,328, for "Nanoparticulate Diagnostic Diatrizoxy Ester X-Ray Contrast Agents for Blood Pool and Lymphatic Systems Imaging;" U.S. Pat. No. 5,534,270, for "Method of Preparing X-Ray Contrast Compositions Containing Nanoparticles;" U.S. Pat. No. 5,573,749, for "Nanoparticulate Diagnostic Mixed Carboxylic Anhydrides as X-Ray Contrast Agents for Blood Pool and Lymphatic System Imaging;" U.S. Pat. No. 5,573,750, for "Diagnostic Imaging X-Ray Contrast Agents;" U.S. Pat. No. 5,603,916, for "3,5-Bis-[Alkanoyl Amino]-2,4,6-Triiodobenzyl Esters;" U.S. Pat. No. 5,643,552, for "Nanoparticulate Diagnostic Mixed Carbonic Anhydrides as X-Ray Contrast Agents for Blood Pool and Lymphatic System Imaging;" U.S. Pat. No. 5,668,196, for "3-Amido-Triiodophenyl Esters as X-Ray Contrast Agents;" and U.S. Pat. No. 5,670,136, for "2,4,6-Triiodo-5-Substituted-Amino-Isophthalate Esters Useful as X-Ray Contrast Agents for Medical Diagnostic Imaging."

U.S. Pat. No 5,585,108, for "Formulations of Oral Gastrointestinal Therapeutic Agents in Combination with Pharmaceutically Acceptable Clays," claims a nanoparticulate dispersion including, inter alia, a water-insoluble particulate drug, a surfactant which can be a polymeric stabilizer, such as hydroxypropyl methylcellulose, a pharmaceutically acceptable clay, and a secondary stabilizer, such as DOSS or sodium lauryl sulfate. See col. 7 of the patent. This reference differs from the present invention in that it is directed to a nanoparticulate dispersion, and not a solid dose nanoparticulate formulation.

U.S. Pat. No 5,298,262, for "Use of Ionic Cloud Point Modifiers to Prevent Particle Aggregation During Sterilization," describes the use of DOSS in a nanoparticulate composition as an anionic surfactant useful in raising the cloud point of a surface stabilizer. According to the '262 patent, by raising the cloud point of the surface stabilizer of a nanoparticulate composition, the composition can be heat sterilized without producing particle aggregation because of the exposure to elevated temperatures. Liquid compositions are heat sterilized, not powders. This is because sterile products are not manufactured for oral administration because of the cost, complexity, etc. Thus, this patent does not teach or suggest the use of DOSS in a solid dose formulation to increase redispersion of the nanoparticulate composition upon administration to a mammal, such as a human or animal, or reconstitution in an aqueous electrolyte solution.

Finally, U.S. Pat. No. 5,518,738, for "Nanoparticulate NSAID Compositions," describes a nanoparticulate solid dose of an NSAID having a film of polyvinylpyrrolidone (PVP), hygroscopic sugar, and sodium lauryl sulfate adsorbed on the surface of the drug. In the examples of this patent, solid films of the nanoparticulate composition with various redispersants are prepared, including DOSS. In contrast to the present invention, the '738 patent teaches that a solid film of a nanoparticulate drug, DOSS, and PVP shows extremely poor redispersibility. Thus, this reference teaches away from the present invention.

Many of the prior art patents listed above also teach the usefulness of polymeric surface stabilizers for nanoparticulate compositions, such as hydroxypropyl cellulose, hydroxypropyl methyl cellulose, and polyvinylpyrrolidone.

However, the prior art does not teach or suggest the use of synergistic combinations of polymeric surface stabilizers and DOSS in solid dose compositions of nanoparticulate active agents. Nor does the prior art teach or suggest that such synergistic compositions can result in superior redispersion of the nanoparticulate composition upon administration to a mammal, such as a human or animal, or reconstitution in an aqueous electrolyte solution.

B. Background Regarding DOSS

DOSS is an anionic surfactant commercially available from a variety of sources, including Chemax Inc. (Greenville, S.C.), Finetex Inc. (Elmwood Park, N.J.), R. W. Greeff & Co. (Greenwich, Conn.), McIntyre Group Ltd. (Chicago, Ill.), Penta Mfg. Co. (Livingston, N.J.), Rhone-Poulenc Inc. Specialty Chemicals Div., (Cranbury, N.J.), RTD Chemicals Corp. (Hackettown, N.J.), Scher Chemicals Inc. (Clifton, N.J.), Spectrum Quality Products Inc. (Gardena, Calif.), Thornley Co. Inc. (Wilmington, Del.), and Van Waters & Rogers (Kirkland, Wash.). It has the chemical formula $C_{20}H_{37}O_7SNa$ and the following structure:

DOSS is a widely used wetting agent and dispersant. It is a white, waxlike, plastic solid added to powdered gelatins, drink mixes, and cocoas to make them dissolve more quickly and completely in liquids. It is also used as a stabilizer in pharmaceuticals, chewing gums, and canned milks, and is added to shampoos, bath products, and skin cleansers. While the U.S. Food and Drug Administration (FDA) limits the amount of DOSS that can be used in food and drug products, it still rates the compound generally recognized as safe (GRAS). 21 C.F.R. § 172.810.

There is a need in the art for solid dose nanoparticulate compositions exhibiting superior redispersion of the nanoparticulate composition upon administration to a mammal, such as a human or animal, or reconstitution in an aqueous electrolyte solution. The present invention satisfies this need.

SUMMARY OF THE INVENTION

The present invention is directed to the surprising and unexpected discovery that solid dose nanoparticulate compositions comprising at least one polymeric surface stabilizer and DOSS exhibit superior redispersion of the nanoparticulate composition upon administration to a mammal, such as a human or animal, or reconstitution in an aqueous electrolyte solution. The solid dose nanoparticulate compositions comprise at least one poorly soluble active agent, at least one polymeric surface stabilizer adsorbed to the surface of the active agent, and DOSS.

Another aspect of the invention is directed to pharmaceutical compositions comprising a solid dose nanoparticulate composition of the invention. The pharmaceutical composition comprises at least one poorly soluble active agent, at least one polymeric surface stabilizer adsorbed to the surface of the drug, DOSS, and a pharmaceutically acceptable carrier, as well as any desired excipients.

This invention further discloses methods of making a nanoparticulate composition having at least one polymeric surface stabilizer adsorbed on the surface of the active agent and DOSS. Such a method comprises contacting a poorly soluble nanoparticulate active agent with at least one polymeric surface stabilizer and DOSS under time and conditions sufficient to provide a nanoparticle active agent/surface stabilizer/DOSS composition. Some or all of the polymeric surface stabilizers and DOSS can be contacted with the active agent either before, during, or after size reduction of the active agent.

The present invention is further directed to methods of treatment comprising administering to a mammal in need a therapeutically effective amount of a nanoparticulate composition according to the invention.

Both the foregoing general description and the following detailed description are exemplary and explanatory and are intended to provide further explanation of the invention as claimed. Other objects, advantages, and novel features will be readily apparent to those skilled in the art from the following detailed description of the invention.

DETAILED DESCRIPTION OF THE INVENTION

The present invention is directed to the surprising and unexpected discovery that solid dose nanoparticulate compositions having at least one polymeric surface stabilizer and DOSS exhibit dramatically superior redispersion of the nanoparticulate composition upon administration to a mammal, such as a human or animal, or upon reconstitution of a dry powder prepared from a nanoparticulate composition in an aqueous electrolyte solution. The electrolyte concentration should be representative of physiological conditions found in the human body. Representative electrolyte solutions can be, but are not limited to, 0.1, 0.01, or 0.001 N HCL, and/or 0.1, 0.01, or 0.001 M NaCl, and combinations thereof. Of these electrolyte solutions, 0.01 N HCl, 0.1 M NaCl, and combinations thereof are most representative of human physiological conditions.

Prior to the present invention, liquid dispersions and solid dose forms of nanoparticulate compositions were known. One frequent problem of prior art solid dose nanoparticulate compositions was that upon administration to a mammal, such as a human or animal, the nanoparticulate composition would not redisperse, and thus the solid dose composition would lose the benefits afforded by formulating the composition into a nanoparticulate form. This is because nanoparticulate compositions benefit from the small particle size of the active agent; if the active agent does not redisperse into the small particle sizes upon administration, then "clumps" or agglomerated drug particles are formed. With the formation of such agglomerated particles, the bioavailability of the composition drops dramatically below that observed with the liquid dispersion form of the drug.

Most drugs are marketed in a solid dose form, such as a tablet, capsule, etc. This is because such dosage forms are easy to store and transport. In addition, such dosage forms are easily marketed. Patient compliance is high, as compared with injectable forms of drugs. Thus, it is critical to develop solid dose forms of nanoparticulate compositions which exhibit the same benefits observed with the liquid dispersion form of the compositions.

It was discovered that solid dose nanoparticulate compositions having at least one polymeric surface stabilizer and DOSS exhibit dramatic redispersion of the nanoparticulate composition upon administration to a mammal, such as a human or animal, or reconstitution in an aqueous electrolyte solution. DOSS or polymeric stabilizers alone cannot produce highly redispersible solid dose nanoparticulate compositions. In combination, however, the two compounds exhibit a synergistic effect of stabilizing the active agent and resulting in dramatic redispersion of the solid dose nanoparticulate composition upon administration to a mammal, such as a human or animal, or reconstitution in an aqueous electrolyte solution.

Another benefit of the invention is that DOSS is highly tolerated by the human body, in contrast to other dispersants such as SLS, for which the human body has a low tolerance. DOSS can be given to humans in large doses on a chronic basis, as the FDA has approved the use of DOSS as a stool softener at doses of up to 500 mg/daily for adults, and in children over 6 months old up to 75 mg/day. See *Handbook of Pharmaceutical Excipients,* Third Edition, p. 189 (American Pharmaceutical Association, 2000). The dosage of DOSS employed in the present invention is below the threshold amount which produces laxative effects.

The combination of DOSS and a polymeric surface stabilizer was tested on a wide variety of drugs, including Mitogen-Activated protein (MAP) kinase inhibitor, an analgesic, and an angiogenesis inhibitor. Thus, the phenomenon of high redispersibility is not limited to a specific drug or drug class. However, the phenomenon is limited to nanoparticulate compositions comprising at least one polymeric surface stabilizer and DOSS. Other types of surface stabilizers formulated with DOSS, such as ampiphilic stabilizers having hydrophobic and hydrophilic ends, have not been found to produce solid dose compositions having comparable redispersion properties.

A. Nanoparticulate Compositions

The nanoparticulate compositions of the invention comprise a nanoparticulate active agent, such as a drug, having at least one polymeric surface stabilizer adsorbed on the surface thereof and DOSS. The nanoparticulate active agent compositions, comprising a nanoparticulate active agent and at least one polymeric surfactant, have an effective average particle size prior to incorporation in a solid dose form of less than about 1 micron, less than about 800 nm, less than about 600 nm, less than about 400 nm, and less than about 200 nm.

Upon administration to a mammal, such as a human or animal, or reconstitution in an electrolyte solution, the solid dose nanoparticulate composition redisperses such that 90% of the active agent particles have a particle size of less than about (1) 5 microns, when the nanoparticulate dispersion, prior to incorporation into a solid dose form, has an effective average particle size of less than about 1 micron; (2) 4 microns, when the nanoparticulate dispersion, prior to incorporation into a solid dose form, has an effective average particle size of less than about 800 nm; (3) 3 microns, when the nanoparticulate dispersion, prior to incorporation into a solid dose form, has an effective average particle size of less than about 600 nm; (4) 2 microns, when the nanoparticulate dispersion, prior to incorporation into a solid dose form, has an effective average particle size of less than about 400 nm; and (5) 1 micron, when the nanoparticulate dispersion, prior to incorporation into a solid dose form, has an effective average particle size of less than about 200 nm.

1. Drug Particles

The nanoparticles of the invention comprise a therapeutic or diagnostic agent, collectively referred to as a "drug," which is poorly soluble in at least one medium. By "poorly soluble" it is meant that the drug has a solubility in the liquid dispersion medium of less than about 10 mg/mL, and preferably of less than about 1 mg/mL. A therapeutic agent can be a pharmaceutical agent, including biologics such as proteins, peptides, and nucleotides, or a diagnostic agent, such as a contrast agent, including x-ray contrast agents. The drug is preferably present in an essentially pure form, is dispersible in at least one liquid medium, and exists either as a discrete, crystalline phase, or as an amorphous phase. The crystalline phase differs from a non-crystalline or amorphous phase which results from precipitation techniques, such as those described in EP Patent No. 275,796.

The drug can be selected from a variety of known classes of drugs, including, for example, proteins, peptides, nucleotides, anti-obesity drugs, nutriceuticals, corticosteroids, elastase inhibitors, analgesics, anti-fungals, oncology therapies, anti-emetics, analgesics, cardiovascular agents, anti-inflammatory agents, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (antiparkinsonian agents), haemostatics, immuriological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators and xanthines.

The drugs are commercially available and/or can be prepared by techniques known in the art.

2. Surface Stabilizers

Polymeric surface stabilizers useful herein physically adhere to the surface of the nanoparticulate active agent, but do not chemically react with the drug or itself. Individually adsorbed molecules of the surface stabilizer are essentially free of intermolecular cross-linkages.

The polymeric surface stabilizer is adsorbed on the surface of the active agent in an amount sufficient to maintain an effective average particle size of less than about 1 micron. Two or more surface stabilizers can be employed in the compositions and methods of the invention.

Representative examples of suitable polymeric surface stabilizers include, but are not limited to polyvinylpyrrolidone (PVP), cellulose ethers such as, but not limited to, hydroxypropyl cellulose, hydroxypropyl methylcellulose, carboxymethyl cellulose, methyl cellulose, and hydroxyethyl cellulose, polysaccharides such as, but not limited to, dextrin, guar gum, starch, random copolymers of vinyl acetate and vinyl pyrrolidone, such as Plasdone® S630 (ISP), Kollidone® VA 64 (BASF), polyvinyl alcohol, copolymers of vinylacetate and vinylalcohol.

Plasdone® S630 is a random copolymer of vinyl pyrrolidone and vinyl acetate, in a 60:40 ratio. Other random copolymers of vinyl pyrrolidone and vinyl acetate can also be used in the invention having, for example, ratios of vinyl pyrrolidone to vinyl acetate of 90:10, 80:20, or 50:50. Preferably, the random copolymer contains at least 50% vinyl pyrrolidone.

The surface stabilizers are commercially available and/or can be prepared by techniques known in the art.

3. Nanoparticulate Dru/Surface Stabilizer Particle Size

As used herein, particle size is determined on the basis of the weight average particle size as measured by conventional particle size measuring techniques well known to those skilled in the art. Such techniques include, for example, sedimentation field flow fractionation, dynamic and static light scattering, and disk centrifugation.

By "an effective average particle size of less than about 1 micron" it is meant that at least 90% of the active agent particles have a particle size of less than about 1 micron when measured by the above techniques. In other embodiments, the nanoparticulate active agent compositions, comprising a nanoparticulate active agent and at least one polymeric surfactant, have an effective average particle size prior to incorporation in a solid dose form of less than about 800 nm, less than about 600 nm, less than about 400 nm, and less than about 200 nm.

Upon administration to a mammal, such as a human or animal, or reconstitution in an electrolyte solution, the solid dose nanoparticulate composition redisperses such that 90% of the active agent particles have a particle size of less than about (1) 5 microns, when the nanoparticulate dispersion, prior to incorporation into a solid dose form, has an effective average particle size of less than about 1 micron; (2) 4 microns, when the nanoparticulate dispersion, prior to incorporation into a solid dose form, has an effective average particle size of less than about 800 nm; (3) 3 microns, when the nanoparticulate dispersion, prior to incorporation into a solid dose form, has an effective average particle size of less than about 600 nm; (4) 2 microns, when the nanoparticulate dispersion, prior to incorporation into a solid dose form, has an effective average particle size of less than about 400 nm; and (5) 1 micron, when the nanocrystal dispersion, prior to incorporation into a solid dose form, has an effective average particle size of less than about 200 nm.

4. Other Pharmaceutical Excipients

Pharmaceutical compositions according to the invention may also comprise one or more binding agents, filling agents, lubricating agents, suspending agents, sweeteners, flavoring agents, preservatives, buffers, wetting agents, disintegrants, effervescent agents, and other excipients. Such excipients are known in the art.

Examples of filling agents are lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicifized microcrystalline cellulose (SMCC).

Suitable lubricants, including agents that act on the flowability of the powder to be compressed, are colloidal silicon dioxide, such as Aerosil® 200, talc, stearic acid, magnesium stearate, calcium stearate, and silica gel.

Examples of sweeteners are any natural or artificial sweetener, such as sucrose, xylitol, sodium saccharin, cyclamate, aspartame, and accsulfame K. Examples of flavoring agents are Magnasweet® (trademark of MAFCO), bubble gum flavor, and fruit flavors, and the like.

Examples of preservatives are potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quarternary compounds such as benzalkonium chloride.

Suitable diluents include pharmaceutically acceptable inert fillers, such as microcrystalline cellulose, lactose, dibasic calcium phosphate, saccharides, and/or mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include corn starch, potato starch, maize starch, and modified starches, croscarmellose sodium, crosspovidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the acid component of the effervescent couple may be present.

5. Concentration of Nanoparticulate Drug, Surface Stabilizer, and DOSS

The relative amount of drug, one or more polymeric surface stabilizers, and DOSS can vary widely. The optimal amount of the polymeric surface stabilizers can depend, for example, upon the particular drug selected, the equivalent hydrophilic lipophilic balance (HLB) of the drug, the melting point, cloud point, and water solubility of the polymeric surface stabilizer, and the surface tension of water solutions of the stabilizer, etc.

The concentration of the one or more polymeric surface stabilizers can vary from about 0.01 to about 90%, from about 1 to about 75%, from about 10 to about 60%, or from about 10 to about 55% by weight based on the total combined dry weight of the drug substance and surface stabilizer, not including other excipients.

The concentration of the drug can vary from about 99.8% to about 0.1%, from about 80% to about 5.0%, or from about 50% to about 10% by weight based on the total combined dry weight of the drug and polymeric surface stabilizer, not including other excipients.

The concentration of DOSS can vary from about 0.1 to about 20%, and from about 1 to about 10%, based on the total dry weight of the drug, surface stabilizer, and DOSS, not including other excipients.

B. Methods of Making Nanoparticulate Formulations

The nanoparticulate drug compositions can be made using, for example, milling or precipitation techniques. Exemplary methods of making nanoparticulate compositions are described in the '684 patent.

1. Milling to obtain Nanoparticulate Drug Dispersions

Milling of aqueous drug dispersions to obtain a nanoparticulate dispersion comprises dispersing poorly soluble drug particles in a liquid dispersion medium, followed by applying mechanical means in the presence of grinding media to reduce the particle size of the drug to the desired effective average particle size. The drug particles can be reduced in size in the presence of at least one polymeric surface stabilizer and/or DOSS. Alternatively, the drug particles may be contacted with one or more polymeric surface stabilizers and/or DOSS after attrition. Other compounds, such as a diluent, can be added to the drug/surface stabilizer composition during the size reduction process. Dispersions can be manufactured continuously or in a batch mode. The resultant nanoparticulate drug dispersion can be utilized in solid dosage formulations, such as controlled release dosage formulations, solid dose fast melt formulations, aerosol formulations, tablets, capsules, etc.

2. Precipitation to Obtain Nanoparticulate Drug Compositions

Another method of forming the desired nanoparticulate composition is by microprecipitation. This is a method of preparing stable dispersions of poorly soluble drugs in the presence of one or more polymeric surface stabilizers and one or more colloid stability enhancing surface active agents free of any trace toxic solvents or solubilized heavy metal impurities. Such a method comprises, for example: (1) dissolving the poorly water-soluble drug in a suitable solvent; (2) adding the formulation from step (1) to a solution comprising at least one polymeric surface stabilizer and DOSS to form a solution; and (3) precipitating the formulation from step (2) using an appropriate non-solvent. The method can be followed by removal of any formed salt, if present, by dialysis or diafiltration and concentration of the dispersion by conventional means. The resultant nanoparticulate drug dispersion can be dried and used in a solid dose composition.

3. Methods of Drying Nanoparticulate Dispersions

The nanoparticulate liquid dispersion formed by either milling or precipitation can be dried prior to formulating the composition into a solid dose form for administration.

Powders comprising nanoparticulate drug can be made by spray-drying aqueous dispersions of a nanoparticulate drug, polymeric surface stabilizer, and DOSS to form a dry powder which consists of aggregated drug/polymeric surface stabilizer/DOSS nanoparticles. Alternatively, the aqueous dispersion of drug, polymeric surface stabilizer, and DOSS can contain a dissolved diluent, such as lactose or mannitol, which when spray dried forms diluent particles, each of which contains at least one embedded drug nanoparticle combined with a polymeric surface stabilizer and DOSS.

Nanoparticulate drug dispersions can also be freeze-dried to obtain powders suitable for formulation into solid dose forms. Such powders comprise aggregated nanoparticulate drug particles having a polymeric surface stabilizer and DOSS. Freeze dried powders can also be obtained by freeze drying aqueous dispersions of drug, polymeric surface stabilizer, and DOSS, which additionally contain a dissolved diluent such as lactose or mannitol. In these instances the freeze dried powders consist of particles of diluent, each of which contains at least one embedded drug nanoparticle combined with a polymeric surface stabilizer and DOSS.

Other known methods of processing liquid dispersions, and which can be employed in the present invention, include granulation, including but not limited to high shear granulation, fluid bed granulation, roto granulation, and melt granulation. Additional methods such as spray coating and extrusion spherization can also be used. Any other conventional method for drying or otherwise processing a liquid dispersion can also be used in the invention.

C. Methods of Using Nanoparticulate Drug Formulations Comprising One or More Polymeric Surface Stabilizers and DOSS The solid dose nanoparticulate compositions of the present invention can be administered to humans and animals in any pharmaceutically acceptable manner, such as orally, rectally, pulmonary, intravaginally, locally (powders, ointments or drops), or as a buccal or nasal spray. Solid dosage forms for oral administration include capsules, tablets, pills, powders, pellets, and granules. In such solid dosage forms, the nanoparticulate drug is admixed with at least one of the following: (a) one or more inert excipients (or carrier), such as sodium citrate or dicalcium phosphate; (b) fillers or extenders, such as starches, lactose, sucrose, glucose, mannitol, and silicic acid; (c) binders, such as carboxymethylcellulose, alignates, gelatin, polyvinylpyrrolidone, sucrose and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as cetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, or mixtures thereof. For capsules, tablets, and pills, the dosage forms may also comprise buffering agents.

Actual dosage levels of the drug in the nanoparticulate compositions of the invention may be varied to obtain an amount of active ingredient that is effective to obtain a desired therapeutic response for a particular composition and method of administration. The selected dosage level therefore depends upon the desired therapeutic effect, the route of administration, the potency of the drug, the desired duration of treatment, and other factors.

The following examples are given to illustrate the present invention. It should be understood, however, that the invention is not to be limited to the specific conditions or details described in these examples. Throughout the specification, any and all references to a publicly available document, including a U.S. patent, are specifically incorporated by reference.

EXAMPLE 1

The purpose of this example was to compare the redispersion properties of various solid dose nanoparticulate ketoprofen compositions in which DOSS is added to a nanoparticulate dispersion following milling and spray drying (rather than during the milling process). Ketoprofen, also known as m-benzoylhydratopic acid, is a nonsteroidal anti-inflammatory analgesic.

A ketoprofen nanoparticulate dispersion was prepared, having 15% ketoprofen, 1.5% PVP K29/32, and 0.075% SLS. The dispersion was prepared using a Dyno®—Mill (Type: KDL; Mfg.: Willy A Bachofen AG, Basel, Switzerland) equipped with a 150 cc batch chamber using a 500 μm milling media of type Polymill500® for 2 hrs at 10° C.

The ketoprofen nanoparticulate dispersion (ketoprofen NCD) was then spray dried with various excipients, as shown in Table 1, using a Büchi Mini Spray Dryer B-191 (Büchi Switzerland). Following spray drying, the redispersion properties of each spray dried ketoprofen powder were tested by measuring the ketoprofen particle size following redispersion and dilution with saturated ketoprofen solution, without sonication and following 1 minute sonication. Particle size was measured using a Horiba LA910 particle sizer. The results of the redispersion tests are also shown in Table 1, below.

TABLE 1

Redispersion Comparison of Nanoparticulate Ketoprofen Spray Dried Powder

| Composition Formula | Redispersed Particle Size (nm) (No sonication/1 min. sonication) | | |
|---|---|---|---|
| | Mean | D90* | % under 1000 nm |
| A no additives | 3801/3725 | 7697/7152 | 12.8/12.8 |
| B Drug:mannitol 1:1.2 | 6836/4050 | 15415/11173 | 41.8/52.2 |
| C Drug:Mannitol:DOSS 1:1.2:0.08 | 1860/1055 | 8785/453 | 84.6/90.1 |
| D Drug:Maltrin150** 1:1.2 | 20665/6104 | 38879/14479 | 9.2/26.6 |
| E Drug:Mannitol:DOSS 1:0.6:0.08 | 17149/2737 | 72756/10229 | 55.4/75.0 |
| F Drug:Xylitol 1:1 | 11241/5277 | 43502/12536 | 65.0/67.8 |
| G Drug:Xylitol:DOSS 1:1:0.08 | 1936/501 | 390/269 | 90.2/95.6 |
| H Drug:Mannitol:DOSS 1:1:0.08 | 4069/1944 | 15113/8313 | 72.6/80.0 |

TABLE 1-continued

Redispersion Comparison of Nanoparticulate Ketoprofen Spray Dried Powder

| Composition Formula | Redispersed Particle Size (nm) (No sonication/1 min. sonication) | | |
|---|---|---|---|
| | Mean | D90* | % under 1000 nm |
| I Drug:Xylitol:DOSS 1:1:0.02 | 11469/2168 | 42333/7702 | 64.1/75.2 |
| J Drug:Mannitol:DOSS 1:1:0.08 | 2963/2004 | 10800/8011 | 72.2/77.5 |
| K Drug:Xylitol:DOSS 1:0.75:0.08 | 654/332 | 273/251 | 95.0/98.2 |

*90% of the particles are below this size.
**maltodextrin

The results dramatically show the effect DOSS has on the redispersibility of the spray dried nanoparticulate ketoprofen composition. Following redispersion, less than 13% of the ketoprofen particles of Composition A, lacking any additives (i.e., just spray dried ketoprofen NCD), had a particle size of less than a micron. Similarly, following redispersion less than 52.2% (following sonication) of the ketoprofen particles of Composition B, containing only mannitol as an additive, had a particle size of less than a micron. In contrast, following redispersion 90.1% (following sonication) of the ketoprofen particles of Composition C, containing mannitol and DOSS as additives, had a particle size of less than a micron. Thus, DOSS resulted in a 75% increase in the amount of particles having a particle size of under 1 micron following redispersion. This is significant as smaller drug particles result in greater bioavailability of the drug.

The amount of DOSS in relation to other excipients also affects the redispersion properties of the solid dose nanoparticulate drug composition. Thus, by varying the amount of DOSS and other excipients, redispersion of a solid dose nanoparticulate composition can be optimized. For example, Composition C, having a Drug:Mannitol:DOSS ratio of 1:1.2:0.08 showed 90.1% of the ketoprofen particles (following sonication) having a particle size of less than 1 micron following redispersion. However, Composition E, having a Drug:Mannitol:DOSS ratio of 1:0.6:0.08, showed 75.0% of the ketoprofen particles (following sonication) having a particle size of less than 1 micron following redispersion; Compositions H and J, having a Drug:Mannitol:DOSS ratios of 1:1:0.08, showed 80.0% and 77.5%, respectively, of the ketoprofen particles (following sonication) having a particle size of less than 1 micron following redispersion.

Similar results were obtained with spray dry excipients other than mannitol. For example, Composition F, having a Drug:Xylitol ratio of 1:1, showed 67.8% of the ketoprofen particles (following sonication) having a particle size of less than 1 micron following redispersion. In contrast, Compositions G and K, having Drug:Xylitol:DOSS ratios of 1:1:0.08 and 1:0.75:0.08, respectively, showed 95.6% and 98.2%, respectively, of the ketoprofen particles (following sonication) having a particle size of less than 1 micron following redispersion. This is an increase of 41% (Composition G) and 45% over the results obtained with Composition F, lacking DOSS.

This example demonstrates the effectiveness of adding DOSS to form a highly redispersible solid dose nanoparticulate composition, when DOSS is added following milling but before spray drying of the nanoparticulate dispersion. Other examples demonstrate the addition of DOSS to the nanoparticulate dispersion during milling. Thus, the time of addition of DOSS during preparation of the pharmaceutical composition is not critical to the goal of obtaining a highly redispersible composition.

EXAMPLE 2

The purpose of this example was to evaluate the redispersion properties of a solid dose nanoparticulate ketoprofen composition comprising DOSS and a polymeric stabilizer in an electrolyte solution. This example differs from Example 1 in that DOSS is added directly to the nanoparticulate dispersion (NCD) during milling, followed by preparation of a solid dose composition.

A ketoprofen nanoparticulate dispersion was prepared, having the composition 5% ketoprofen, 1.% PVP K29/32, and 0.2% DOSS. The dispersion was prepared using a Dyno®—Mill (Type: KDL; Mfg.: Willy A Bachofen AG, Basel Switzerland) equipped with a 150 cc batch chamber using a 500 μm milling media of type Polymill500® for 2 hrs at 10° C.

The ketoprofen nanoparticulate dispersion (ketoprofen NCD) was then spray dried with mannitol, with a drug to mannitol ratio of 1:1 using a Büchi Mini Spray Dryer B-191 (Büchi Switzerland). The redispersion properties of the spray dried ketoprofen in water are shown below in Table 2.

stomach, the pH ranges from slightly less than 2 (but typically greater than 1) up to 4 or 5. In the small intestine the pH can range from 4 to 6, and in the colon it can range from 6 to 8. Thus, a 0.01 N HCl concentration simulates typical acidic conditions found in the stomach. 0.1 M NaCl simulates the electrolyte concentration found throughout the body, including the intestine.

The results show that under acidic to neutral pH conditions, the nanoparticulate ketoprofen solid dose composition showed excellent redispersion properties, with 100% of the nanoparticulate particles having a redispersed particle size of less than 1 micron. In addition, under all but the most acidic conditions of 0.1 M HCl (which are not typically representative of human gastric pH), the nanoparticulate ketoprofen solid dose composition showed excellent redispersion properties, with almost 100% of the nanoparticulate particles having a redispersed particle size of less than 1 micron.

EXAMPLE 3

The purpose of this example was to evaluate the redispersion properties of a solid dose nanoparticulate MAP kinase inhibitor composition comprising DOSS and a polymeric stabilizer in electrolyte solutions.

TABLE 2

Redispersion Properties of Ketoprofen Spray Dried NCD Containing DOSS in Water

| Time (days) | Mean (no sonication) | Mean (1 min. sonication) | $D_{50}$ (1 min. sonication) | $D_{50}$ (no sonication) | $D_{90}$ (1 min. sonication) | $D_{90}$ (no sonication) |
|---|---|---|---|---|---|---|
| 0 | 118 | 121 | 105 | 107 | 192 | 198 |
| 1 | 152 | 163 | 144 | 155 | 219 | 233 |

All measurements are in nanometers (nm).

The results of the redispersion test show excellent redispersion of the spray dried nanoparticulate ketoprofen composition comprising DOSS.

The redispersion properties of the same spray dried ketoprofen composition were then tested in electrolyte solutions, which mimic the conditions found in the human gastrointestinal tract. The results of these tests are shown in Table 3, below.

5% (w/w) of Compound A, a MAP kinase inhibitor, 1% Plasdone® S630, and 0.2% DOSS were milled using a Dyno®—Mill (Type: KDL; Mfg.: Willy A Bachofen AG, Basel Switzerland) equipped with a 150 cc batch chamber using a 500 μm milling media of type Polymill500® for 3 hrs at 10° C.

The nanoparticulate MAP kinase inhibitor dispersion (NCD) was then spray dried at a drug to mannitol ratio of 1:1

TABLE 3

Redispersion Properties of Ketoprofen Spray Dried NCD Comprising DOSS in an Electrolyte Solution

| Electrolyte Conc. (M) | Type | no sonic. Mean | No sonic. Small % | No sonic. Large % | 1 min. sonic. Mean | 1 min. sonic. Small % | No. sonic. Large % |
|---|---|---|---|---|---|---|---|
| 0 | — | 172 | 100 | 0 | 182 | 100 | 0 |
| 0.001 | HCl | 535 | 97 | 3 | 166 | 100 | 0 |
| 0.01 | HCl | 176 | 100 | 0 | 188 | 100 | 0 |
| 0.1 | HCl | 17756 | 2 | 98 | 5908 | 8 | 92 |
| 0.001 | NaCl | 178 | 100 | 0 | 191 | 100 | 0 |
| 0.01 | NaCl | 151 | 100 | 0 | 163 | 100 | 0 |
| 0.1 | NaCl | 186 | 100 | 0 | 204 | 100 | 0 |

All particle sizes are in nanometers (nm).

Figure 1:
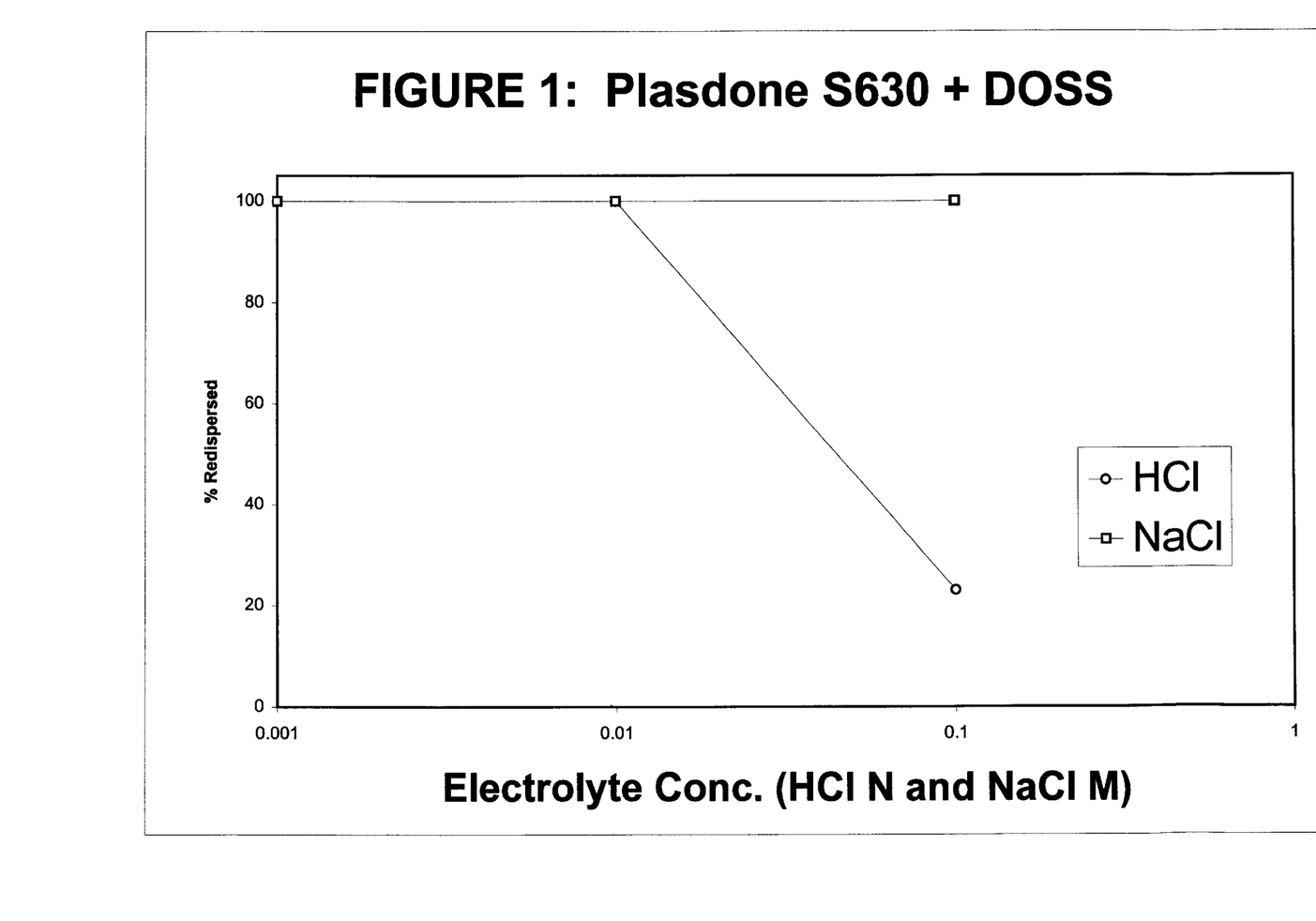
FIG. 1: Shows the % redispersion in an electrolyte solution, as a function of the concentration of the electrolyte solution, for a spray dried nanoparticulate MAP kinase inhibitor composition.

"Small" particles are defined as those below 1 micron (1000 nm) and "large" particles are those above 1 micron. Electrolyte concentrations of 0.001 HCl, 0.01 HCl, and 0.1 HCl correspond to pH 3, pH 2, and pH 1, respectively. In the using a Büchi Mini Spray Dryer B-191 (Büchi Switzerland). The redispersion properties of the spray dried MAP kinase inhibitor in electrolyte solutions are shown below in Table 4 and in FIG. 1. A Horiba LA910 particle sizer was used to measure particle size. "Small" particles were defined as those below 1 micron and "large" particles were defined as those above 1 micron.

TABLE 4

Redispersion Properties of a MAP Kinase Inhibitor Spray Dried NCD Comprising DOSS and a Polymeric Stabilizer in an Electrolyte Solution

| Electrolyte Conc. (M) | Type | no sonic. Mean | No sonic. Small % | No sonic. Large % | 1 min. sonic. Mean | 1 min. sonic. Small % | No. sonic. Large % |
|---|---|---|---|---|---|---|---|
| 0 | — | 99 | 100 | 0 | 99 | 100 | 0 |
| 0.001 | HCl | 100 | 100 | 0 | 100 | 100 | 0 |
| 0.01 | HCl | 105 | 100 | 0 | 106 | 100 | 0 |
| 0.1 | HCl | 4708 | 23 | 77 | 1901 | 52 | 48 |
| 0.001 | NaCl | 103 | 100 | 0 | 103 | 100 | 0 |
| 0.01 | NaCl | 101 | 100 | 0 | 101 | 100 | 0 |
| 0.1 | NaCl | 105 | 100 | 0 | 105 | 100 | 0 |

All particle sizes are in nanometers (nm).

The results show that the solid dose nanoparticulate MAP kinase inhibitor composition, comprising DOSS and a polymeric stabilizer, showed excellent redispersion in all tested electrolyte media representative of in vivo conditions. Even at a higher acid concentration of 0.1 N HCl, the composition showed over 50% of the drug particles of the composition having a small particle size following 1 minute of sonication.

EXAMPLE 4

The purpose of this example was to evaluate the redispersion properties of a solid dose nanoparticulate angiogenesis inhibitor composition comprising DOSS and a polymeric stabilizer, which has been spray granulated with various excipients, in water and in electrolyte solutions.

Nanocrystalline dispersions (NCD) of an angiogenesis inhibitor, Compound C, were made by milling the ingredients shown for each composition in Table 7. Samples A and B were milled on a Netzch Mill (Netzsch Inc., Exton, Pa.), having a LMZ 2L chamber, for 11 hrs. 500 micron PolyMill media was used. Processing temperatures ranged from 11.6° C. to 27.4° C. Samples C–E were milled on a Dyno® Mill, having a 150 cc chamber, at a temperature of 10° C. for 3 hours, also using 500 micron PolyMill media.

Following milling, the additives listed in Table 5 were added to the nanoparticulate dispersion until dissolved, followed by spraying of the dispersion over a fluidized mannitol excipient, also provided in Table 5, to form a solid dose composition. A Glatt GPCG-1 fluid bed processor (Glatt Air Technologies, Inc., Ramsey, N.J.) was used for this process.

TABLE 5

Spray Granulated Nanoparticulate Angiogenesis Inhibitor Compositions

| Sample | Formula | Particle Size of Nanocrystal Dispersion (nm) | Additives | Fluidized Mannitol |
|---|---|---|---|---|
| A | 15% Drug + 3.75% PVP K29/32 and 0.15% SLS | mean 105 nm; $D_{90}$ of 167 nm | Drug:mannitol ratio of 1:0.75 | Pearlitol ® SD200 |
| B | 15% Drug + 3.75% PVP K29/32 and 0.15% SLS | mean 105 nm; $D_{90}$ of 167 nm | Drug:mannitol ratio of 1:0.75 | Pearlitol ® SD200 |
| C | 15% Drug + 3.75% PVP K29/32, 0.15% SLS, and 0.1% sodium ascorbate | mean of 101 nm; $D_{90}$ of 165 nm | Drug:mannitol ratio of 1:0.75 | Mannitol 35 |
| D | 15% Drug + 3.75% PVP K29/32, 0.15% SLS, and 0.1% sodium ascorbate | mean of 101 nm; $D_{90}$ of 165 nm | Drug:mannitol ratio of 1:0.75 | Mannitol 35 |
| E | 15% Drug + 3.75% PVP K29/32, 0.15% SLS, and 0.1% sodium ascorbate | mean of 101 nm; $D_{90}$ of 165 nm | Drug:mannitol ratio of 1:0.75 and stabilizer DOSS ratio of 1:0.2 | Mannitol 35 |

Each composition A–E, comprising drug/excipient granules, was then milled to a uniform particle size in a Quadro Comill (Model 193; also called a cone mill, which comprises fixed stationary screens and a rotating impeller), to produce Compositions A2–E2. The milling process comprised passing the powder through the mill (one pass through, about 2–5 minutes).

The redispersibility, in water and various electrolyte solutions, was then measured for the solid dose nanoparticulate angiogenesis compositions, both Compositions A–E (unmilled) and A2–E2 (milled), as shown in Table 6.

TABLE 6

Redispersibility of Spray Granulated Nanoparticulate Angiogenesis Inhibitor Compositions (Milled and Unmilled Granulate Compositions)

| Composition | Redisp. Media | No Sonication | | | 1 Min. Sonication | | |
|---|---|---|---|---|---|---|---|
| | | Mean (nm) | D90 (nm) | % Under 1000 nm | Mean (nm) | D90 (nm) | % Under 1000 nm |
| A (unmilled) | water | 5265 | 11776 | 26.2 | 1440 | 4717 | 70.8 |
| | 0.01 N HCl | 12160 | 27244 | 9.4 | 3034 | 6997 | 36.1 |
| | 0.01 M NaCl | 7487 | 15324 | 11.6 | 2274 | 6504 | 57.6 |
| A2 (milled) | water | 5777 | 12463 | 23.0 | 2538 | 7547 | 62.9 |
| | 0.01 M N HCl | 58519 | 236602 | 5.3 | 3573 | 7929 | 30 |
| | 0.01 M NaCl | 8341 | 17698 | 11 | 1975 | 5366 | 54.9 |
| B (unmilled) | water | 8222 | 18365 | 18.5 | 4368 | 9033 | 51.5 |
| | 0.01 N HCl | 83643 | 264545 | 4.8 | 4238 | 9458 | 26.3 |
| | 0.01 M NaCl | 14863 | 331391 | 8 | 2579 | 6561 | 45.8 |
| B2 (milled) | water | 18897 | 55523 | 14.2 | 2691 | 7294 | 50 |
| | 0.01 N HCl | 44037 | 103747 | 4.1 | 5161 | 1771 | 22.4 |
| | 0.01 M NaCl | 13514 | 29820 | 6.8 | 2547 | 6163 | 42.1 |
| C (unmilled) | water | 3124 | 8088 | 46.9 | 422 | 645 | 93.4 |
| | 0.01 N HCl | 6713 | 14117 | 16.6 | 2471 | 6285 | 47 |
| | 0.01 M NaCl | 4103 | 9426 | 30.6 | 904 | 3006 | 80.4 |
| C2 (milled) | water | 3150 | 8427 | 49 | 1071 | 3602 | 83.6 |
| | 0.01 N HCl | 8728 | 19180 | 17.1 | 3039 | 7626 | 43.3 |
| | 0.01 M NaCl | 4544 | 9896 | 25.5 | 1278 | 4345 | 75 |
| D (unmilled) | water | 3094 | 7865 | 44.8 | 342 | 569 | 97.3 |
| | 0.01 N HCl | 9630 | 21697 | 14.8 | 2762 | 7043 | 45.3 |
| | 0.01 M NaCXl | 4295 | 8561 | 20.6 | 1475 | 5034 | 73.6 |
| D2 (milled) | water | 2162 | 5885 | 54.4 | 295 | 488 | 98.7 |
| | 0.01 N HCl | 8885 | 20181 | 16.9 | 1982 | 5087 | 51.7 |
| | 0.01 M NaCl | 4410 | 8710 | 19 | 1066 | 3420 | 75.9 |
| E (unmilled) | water | 2186 | 7520 | 69.9 | 384 | 614 | 98.3 |
| | 0.01 N HCl | 2161 | 7812 | 73.4 | 297 | 492 | 99 |
| | 0.01 M NaCl | 2544 | 8755 | 68.1 | 357 | 588 | 98.5 |
| E (milled) | water | 2711 | 9141 | 66.6 | 436 | 672 | 93.6 |
| | 0.01 N HCl | 2014 | 7608 | 75.9 | 291 | 483 | 99.1 |
| | 0.01 M NaCl | 2203 | 8075 | 74.1 | 292 | 484 | 99 |

Only Sample E comprises DOSS. The redispersibility results showed that only this sample showed substantially improved redispersion in electrolyte media, with a redispersibility of 99.1% in 0.01 N HCl and 99% in 0.01 M NaCl. In contrast, Samples A–D showed redispersibility in 0.01 N HCl of from 22.4% (Sample B2) to 51.7% (Sample D2), and a redispersibility in 0.01 N HCl of from to 42.1% (Sample B2) to 80.4% (Sample C). The results are dramatic as the only difference between Sample E and Samples C and D was the presence (Sample E) or absence (Samples C and D) of DOSS.

The results demonstrate the dramatically superior redispersibility properties of a solid dose nanoparticulate formulation comprising DOSS.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

We claim:

1. A solid dose nanoparticulate composition comprising:

(a) an active agent which has a solubility in a liquid dispersion medium of less than about 10 mg/mL;

(b) at least one polymeric surface stabilizer adsorbed on the surface of the active agent; and (c) about 0.1% to about 20% w/w, of dioctyl sodium sulfosuccinate (DOSS), wherein the effective average particle size of the nanoparticulate dispersion prior to incorporation in the solid dose formulation, comprising said poorly soluble active agent and at least one polymeric surface stabilizer, is less than about 1 micron, and upon reconstitution in media representative of human physiological conditions, the solid dose nanoparticulate composition redisperses such that 90% of the active agent particles have a particle size of less than about 5 microns.

2. The composition of claim 1, wherein the active agent is present in an amount of about 99.8% to about 0.1% (w/w).

3. The composition of claim 1, wherein the active agent is present in an amount of about 80% to about 5% (w/w).

4. The composition of claim 1, wherein the active agent is present in an amount of about 50% to about 10% (w/w).

5. The composition of claim 1, wherein the at least one polymeric surface stabilizer is present in an amount of about 0.01% to about 90% (w/w).

6. The composition of claim 1, wherein the at least one polymeric surface stabilizer is present in an amount of about 1% to about 75% (w/w).

7. The composition of claim 1, wherein the at least one polymeric surface stabilizer is present in an amount of about 10% to about 60% (w/w).

8. The composition of claim 1, wherein DOSS is present in an amount of about 1% to about 10% (w/w).

9. The composition of claim 1, wherein the effective average particle size of the nanoparticulate dispersion prior to incorporation in the solid dose formulation, comprising said poorly soluble active agent and at least one polymeric surface stabilizer, is less than about 800 nm, and upon reconstitution in media representative of human physiological conditions, the solid dose nanoparticulate composition redisperses such that 90% of the active agent particles have a particle size of less than about 4 microns.

10. The composition of claim 1, wherein the effective average particle size of the nanoparticulate dispersion prior to incorporation in the solid dose formulation, comprising said poorly soluble active agent and at least one polymeric surface stabilizer, is less than about 600 nm, and upon reconstitution in media representative of human physiological conditions, the solid dose nanoparticulate composition redisperses such that 90% of the active agent particles have a particle size of less than about 3 microns.

11. The composition of claim 1, wherein the effective average particle size of the nanoparticulate dispersion prior to incorporation in the solid dose formulation, comprising said poorly soluble active agent and at least one polymeric surface stabilizer, is less than about 400 nm, and upon reconstitution in media representative of human physiological conditions, the solid dose nanoparticulate composition redisperses such that 90% of the active agent particles have a particle size of less than about 2 microns.

12. The composition of claim 1, wherein the effective average particle size of the nanoparticulate dispersion prior to incorporation in the solid dose formulation, comprising said poorly soluble active agent and at least one polymeric surface stabilizer, is less than about 200 nm, and upon reconstitution in media representative of human physiological conditions, the solid dose nanoparticulate composition redisperses such that 90% of the active agent particles have a particle size of less than about 1 micron.

13. The composition of claim 1, wherein the active agent is selected from the group consisting of a crystalline phase drug, a semi-crystalline phase drug, and an amorphous phase drug.

14. The composition of claim 1, wherein the active agent is selected from the group consisting of proteins, peptides, nucleotides, anti-obesity drugs, nutriceuticals, corticosteroids, elastase inhibitors, analgesics, anti-fungals, oncology therapies, anti-emetics, analgesics, cardiovascular agents, anti-inflammatory agents, anthelmintics, anti-arrhythmic agents, antibiotics, anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives, astringents, beta-adrenoceptor blocking agents, blood products and substitutes, cardiac inotropic agents, contrast media, corticosteroids, cough suppressants, diagnostic agents, diagnostic imaging agents, diuretics, dopaminergics, haemostatics, immuriological agents, lipid regulating agents, muscle relaxants, parasympathomimetics, parathyroid calcitonin and biphosphonates, prostaglandins, radio-pharmaceuticals, sex hormones, anti-allergic agents, stimulants and anoretics, sympathomimetics, thyroid agents, vasodilators, and xanthines.

15. The composition of claim 1, wherein the at least one polymeric surface stabilizer is selected from the group consisting of polyvinylpyrrolidone (PVP), cellulose ethers, polysaccharides, random copolymers of vinyl acetate and vinyl pyrrolidone, polyvinyl alcohol, and copolymers of vinyl acetate and vinyl alcohol.

16. The composition of claim 15, wherein the at least one polymetric surface stabilizer is selected from the group consisting of hydroxypropyl cellulose, hydroxypropyl methylcellulose, carboxymethyl cellulose, methyl cellulose, hydroxyethyl cellulose, dextrin, guar gum, starch, and a copolymer of 1-vinyl-2-pyrrolidone and vinyl acetate in a mass proportion of 3:2.

17. A method of making a solid dose nanoparticulate composition having a high redispersibility upon administration to a mammal comprising:

(a) dispersing particles of an active agent which has a solubility in a liquid dispersion medium of less than about 10 mg/mL in a liquid dispersion medium;

(b) applying mechanical means in the presence of grinding media to reduce the effective average particle size of the active agent in the liquid dispersion medium to less than about 1 micron, wherein at least one polymeric surface stabilizer and dioctyl sodium sulfosuccinate are added to the liquid dispersion medium before or after milling;

(c) drying the nanoparticulate dispersion comprising an active agent, at least one polymeric surface stabilizer, and dioctyl sodium sulfosuccinate; and (d) formulating the dry nanoparticulate composition into a solid dose form for administration, wherein upon reconstitution in media representative of human physiological conditions, the solid dose nanoparticulate composition redisperses such that 90% of the active agent particles have a particle size of less than about 5 microns.

18. The method of claim 17, wherein the active agent is present in an amount of about 99.8 to about 0.1% (w/w).

19. The method of claim 17, wherein the at least one polymeric surface stabilizer is present in an amount of about 0.01% to about 90% (w/w).

20. The method of claim 17, wherein DOSS is present in an amount of about 0.1% to about 20% (w/w).

21. The method of claim 17, wherein DOSS is present in an amount of about 1.0% to about 10% (w/w).

22. The method of claim 17, wherein the active agent is selected from the group consisting of a crystalline phase drug, a semi-crystalline phase drug, and an amorphous phase drug.

23. The method of claim 17, wherein the effective average particle size of the nanoparticulate dispersion prior to incorporation in the solid dose formulation, comprising said poorly soluble active agent and at least one polymeric surface stabilizer, is less than about 800 nm, and upon reconstitution in media representative of human physiological conditions, the solid dose nanoparticulate composition redisperses such that 90% of the active agent particles have a particle size of less than about 4 microns.

24. The method of claim 17, wherein the effective average particle size of the nanoparticulate dispersion prior to incorporation in the solid dose formulation, comprising said poorly soluble active agent and at least one polymeric surface stabilizer, is less than about 600 nm, and upon reconstitution in media representative of human physiological conditions, the solid dose nanoparticulate composition redisperses such that 90% of the active agent particles have a particle size of less than about 3 microns.

25. The method of claim 17, wherein the effective average particle size of the nanoparticulate dispersion prior to incorporation in the solid dose formulation, comprising said poorly soluble active agent and at least one polymeric surface stabilizer, is less than about 400 nm, and upon reconstitution in media representative of human physiological conditions, the solid dose nanoparticulate composition redisperses such that 90% of the active agent particles have a particle size of less than about 2 microns.

26. The method of claim 17, wherein the effective average particle size of the nanoparticulate dispersion prior to incorporation in the solid dose formulation, comprising said poorly soluble active agent and at least one polymeric surface stabilizer, is less than about 200 nm, and upon reconstitution in media representative of human physiological conditions, the solid dose nanoparticulate composition redisperses such that 90% of the active agent particles have a particle size of less than about 1 micron.

27. A method of treating a patient in need with a solid dose nanoparticulate composition having high redispersibility of the nanoparticulate composition upon administration to a mammal, comprising administering to a patient in need a therapeutically effective amount of a solid dose nanoparticulate composition comprising:
  (a) an active agent which has a solubility in a liquid dispersion medium of less than about 10 mg/mL;
  (b) at least one polymeric surface stabilizer adsorbed on the surface of the active agent; and
  (c) about 0.1% to about 20% w/w of dioctyl sodium sulfosuccinate (DOSS),
  wherein the effective average particle size of the nanoparticulate dispersion prior to incorporation in the solid dose formulation, comprising said poorly soluble active agent and at least one polymeric surface stabilizer, is less than about 1 micron, and upon reconstitution in media representative of human physiological conditions, the solid dose nanoparticulate composition redisperses such that 90% of the active agent particles have a particle size of less than about 5 microns.

28. The method of claim 27, wherein the active agent is present in an amount of about 99.8 to about 0.1% (w/w).

29. The method of claim 27, wherein the at least one polymeric surface stabilizer is present in an amount of about 0.01% to about 90% (w/w).

30. The method of claim 27, wherein DOSS is present in an amount of about 1.0% to about 10% (w/w).

31. The method of claim 27, wherein the effective average particle size of the nanoparticulate dispersion prior to incorporation in the solid dose formulation, comprising said poorly soluble active agent and at least one polymeric surface stabilizer, is less than about 800 nm, and upon reconstitution in media representative of human physiological conditions, the solid dose nanoparticulate composition redisperses such that 90% of the active agent particles have a particle size of less than about 4 microns.

32. The method of claim 27, wherein the effective average particle size of the nanoparticulate dispersion prior to incorporation in the solid dose formulation, comprising said poorly soluble active agent and at least one polymeric surface stabilizer, is less than about 600 nm, and upon reconstitution in media representative of human physiological conditions, the solid dose nanoparticulate composition redisperses such that 90% of the active agent particles have a particle size of less than about 3 microns.

33. The method of claim 27, wherein the effective average particle size of the nanoparticulate dispersion prior to incorporation in the solid dose formulation, comprising said poorly soluble active agent and at least one polymeric surface stabilizer, is less than about 400 nm, and upon reconstitution in media representative of human physiological conditions, the solid dose nanoparticulate composition redisperses such that 90% of the active agent particles have a particle size of less than about 2 microns.

34. The method of claim 27, wherein the effective average particle size of the nanoparticulate dispersion prior to incorporation in the solid dose formulation, comprising said poorly soluble active agent and at least one polymeric surface stabilizer, is less than about 200 nm, and upon reconstitution in media representative of human physiological conditions, the solid dose nanoparticulate composition redisperses such that 90% of the active agent particles have a particle size of less than about 1 micron.

* * * * *